United States Patent [19]

Tashiro

[11] Patent Number: 4,827,907
[45] Date of Patent: May 9, 1989

[54] INTRA-OBSERVATION APPARATUS

[75] Inventor: Yoshio Tashiro, Tokyo, Japan

[73] Assignee: Teac Optical Co., Ltd., Tokyo, Japan

[21] Appl. No.: 123,642

[22] Filed: Nov. 20, 1987

[30] Foreign Application Priority Data

Nov. 28, 1986 [JP] Japan ................................ 61-283565

[51] Int. Cl.⁴ .............................................. A61B 1/06
[52] U.S. Cl. ........................................... 128/6; 358/98
[58] Field of Search ........................... 128/4, 6; 358/98

[56] References Cited

U.S. PATENT DOCUMENTS 4,349,014  9/1982  Takamatsu ................................ 128/6
4,576,146  3/1986  Kawazoe et al. ......................... 128/6
4,742,388  5/1988  Cooper ..................................... 358/98

FOREIGN PATENT DOCUMENTS 59-172621  9/1984  Japan .
61-80218   4/1986  Japan .

Primary Examiner—William H. Grieb
Attorney, Agent, or Firm—Ladas & Parry

[57] ABSTRACT

An intra-observation apparatus comprises an endoscope inserted into the blood vessel, a television camera for converting to an image signal an image which is obtained from the distal end of the endoscope, an endoscopic image analyzer for determining the state of observation at a region of interest on the basis of the image signal and an injector device for controlling the level of an injection flow into the blood vessel in accordance with the state of observation at the region of interest. The analyzer determines an occupation area of the blood level on the observation image and the injector device injects into the blood vessel the injection flow level of the liquid in accordance with the blood level.

17 Claims, 6 Drawing Sheets

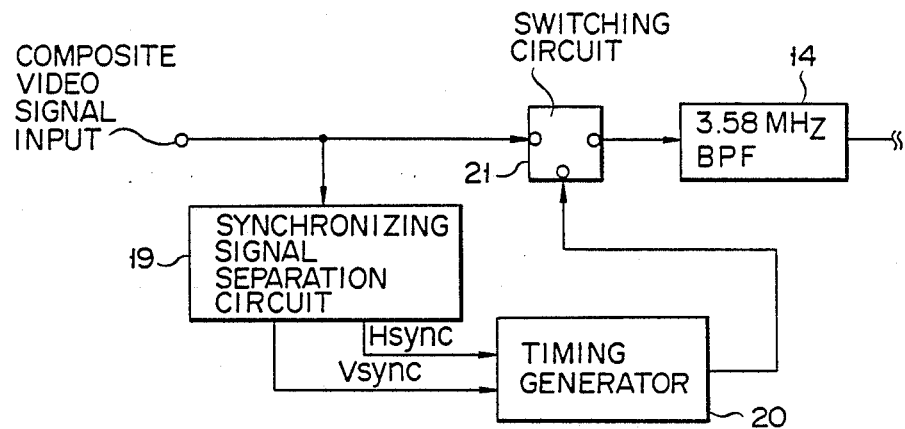
F I G. 4
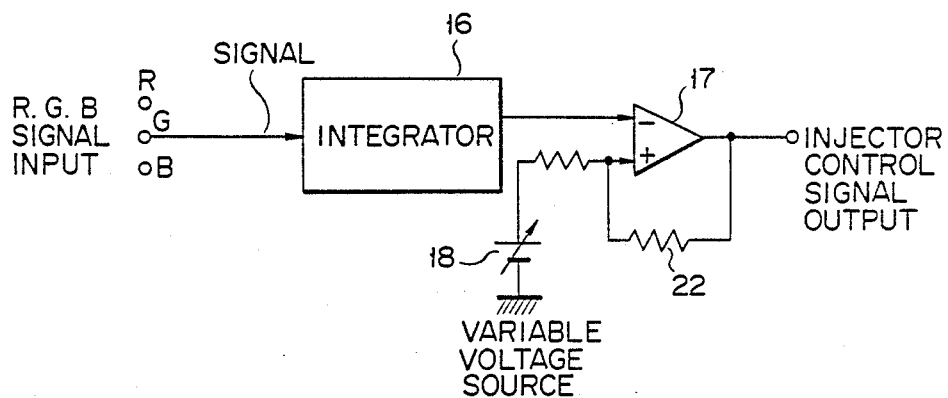
F I G. 5

INTRA-OBSERVATION APPARATUS

BACKGROUND OF THE INVENTION

This invention relates to an intra-observation apparatus for observing the interior of the blood vessel of a human subject.

Recently, a very narrow endoscope has been developed for observing the interior of the blood vessel for the medical treatment of the arterio-sclerosis or the interior of the blood vessel subsequent to the percutaneous transluminal coronary angioplasty or the blood-vessel bypass operation. This type of endoscope is guided to a region of interest (ROI) through a guide sheath which has been inserted into the blood vessel. However, since the blood runs through the blood vessel, it is not possible to observe the state of the inner wall or valve (ROI) of the blood vessel even it is illuminated with illumination light. It is the usual practice to inject a transparent liquid, such as a physiological saline, into a gap between the guide sheath and the endoscope or into a channel provided in the endoscope so that the blood stream at the ROI is locally replaced temporarily with the injected transparent liquid for observation to be made without hindrance. In this case, in order to make continuous observation, it is necessary that the transparent liquid be continuously injected under a certain pressure level into the ROI against the blood stream. As means for injecting the transparent liquid, use is made of a manual injector to allow a transparent liquid to be manually injected into an infusion tube which has been inserted into the injection, or an automatic injector. Such a type of automatic injector is disclosed, for example, in Japanese Patent Disclosure (KOKAI) No. 59-172621, which is adapted to detect a variation in an amount of received light varying in accordance with a variation in the reflection surface of the blood vessel and to automatically control an amount of transparent liquid in accordance with the variation level.

Where the blood stream is locally to be replaced by a transparent liquid with the use of a conventional intra-observation apparatus, if a pressure level is set too low prior to the injection of the transparent liquid, the blood stream is not adequately displaced with a liquid against the blood pressure due to too small a flow of the transparent liquid involved, failing to observe the inner wall of the blood vessel. If the pressure level is set too high, on the other hand, the transparent liquid will be injected into the blood vessel to an extent exceeding a requisite level. Needless to say, it is desirable from the physiological viewpoint that the amount of transparent liquid injected into the blood vessel be as small as required. Furthermore, the amount of transparent liquid required for observation varies, depending upon the inner diameter of the blood vessel at the ROI of the human subject. In the conventional method, a trial and error operation has to be repeated in an attempt to determine an optimum amount of transparent liquid injected, making it necessary to inject an extra liquid into the blood stream.

In the aforementioned conventional apparatus, since the transparent liquid is injected into the blood stream at a fixed level of flow irrespective of the interior state of the blood vessel under observation, various troubles may be caused, from the physiological viewpoint, due to an extra flow of the transparent liquid, thus providing a greater bar to a greater acceptance of the operation using an endoscope.

In this type of apparatus as disclosed in Japanese Patent Disclosure (KOKAI) No. 59-172621, a very complex arrangement is required at the distal end of an endoscope and hence the endoscope is technically difficult to implement. Where such a complex arrangement is adopted at a very narrow endoscope of a type adapted to be inserted into the blood vessel, the insertion section of the endoscope becomes larger in its outer diameter and the resultant endoscope causes a greater burden on the patient. Furthermore, the endoscope detects pressure exerted on, or the flow velocity prevalent at, the distal end of the endoscope. Thus the apparatus cannot determine whether the liquid at the distal end of the endoscope is the blood or the transparent liquid. It is thus impossible to make continuous observation.

SUMMARY OF THE INVENTION

It is accordingly the object of this invention to provide a simpler intra-observation apparatus which, without inflicting any appreciable burden upon a human subject, can observe the interior of the blood vessel by automatically controlling a flow level of transparent liquid, to be injected, in accordance with the interior state of the blood vessel under observation.

According to this invention, an intra-observation apparatus is provided which comprises an endoscope for observing an image of a body cavity of a human subject, imaging means for converting to an image signal an observation image obtained by the endoscope, an image analyzer for evaluating the tonal color of the observation image from the image signal and for outputting an injection control signal corresponding to the tonal color, and control means for controlling in response to the injection control signal the level of a liquid flow to be injected into the blood stream.

BRIEF DESCRIPTION OF THE DRAWINGS

FIG. 4 is a block circuit diagram showing an endoscopic analyzer for use in an intra-observation endoscope according to another embodiment of this invention;

FIG. 5 is a block circuit diagram showing an endoscopic image analyzer for use in an intra-observation endoscope according to another embodiment;

DETAILED DESCRIPTION OF THE PREFERRED EMBODIMENTS

Figure 1:
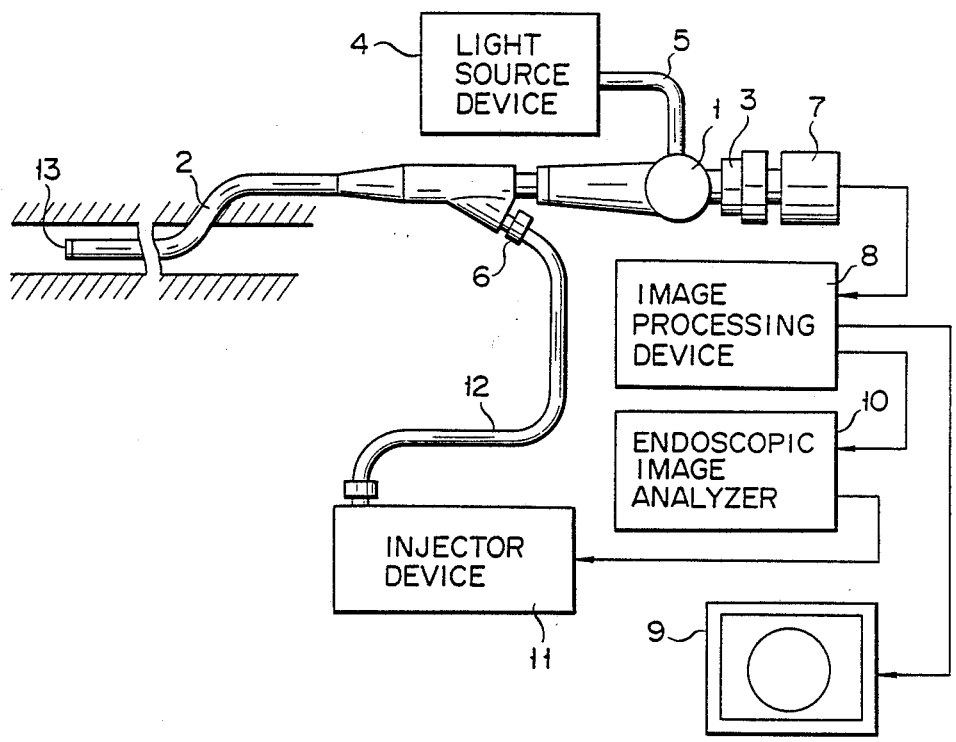
FIG. 1 is a block circuit diagram showing an intra-observation apparatus according to one embodiment of this invention.

As shown in FIG. 1, endoscope 1 has insertion section 2 to be inserted into the blood vessel of a human subject, eyepiece section 3, light source device 4, light guide code 5 connected to light source device 4, and forceps inlet communicating with a channel of the insertion section of the endoscope. Camera 7 is attached to eyepiece section 3 and includes a solid state image sensor or image tube. Camera 7 has its output terminal connected to image processor 8. Image processing apparatus 8 subjects an image signal obtained from camera 7 to a signal processing to output a composite video signal (NTSC signal).

The output terminal of image processing device 8 is connected to television monitor 9 and to endoscopic image analyzer 10. The analyzer delivers an injector control signal corresponding to the state of an endoscopic image, while based on the video signal. The analyzer has its output terminal connected to injector device 11.

Injector device 11 includes a tank for storing a physiological saline so that the saline is sent from the tank by a mechanical pressure level corresponding to an injector control signal. The outlet of injector device 11 is connected to forceps inlet 6 by liquid supply tube 12 for the saline, to be sent from injector device 11 into the endoscope channel past liquid supply tube 12.

Figure 3:
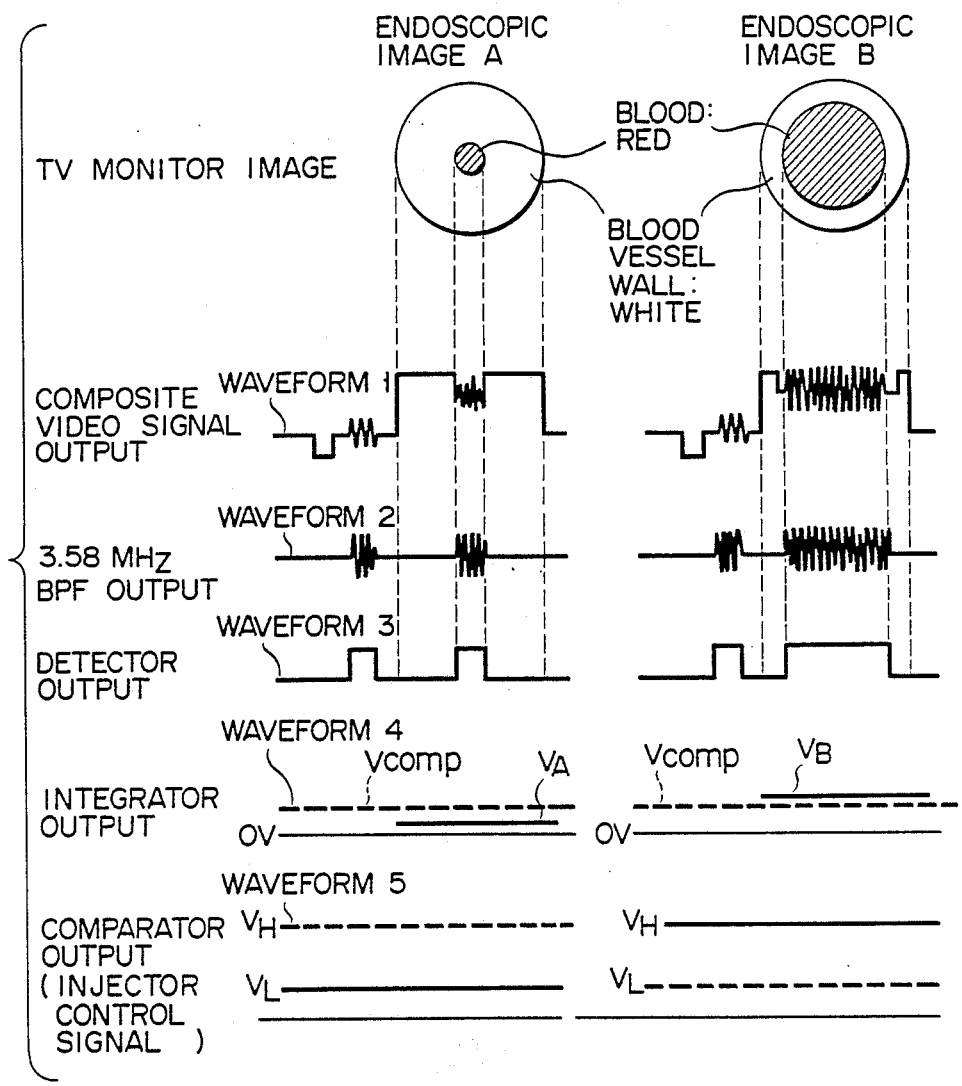
FIG. 3 is a time chart for explaining the operation of the embodiment of FIG. 1.

In the aforementioned embodiment, an image from the distal end of the endoscope is photographed by camera 7 and the image signal is supplied to image processing device 8, which in turn supplies a video signal to monitor 9 where the aforementioned image is displayed. The endoscopic image A as shown in FIG. 3 corresponds to the state in which the blood stream is locally narrowed near the middle of the visual field of the endoscope. This state means that the blood stream is locally replaced by the physiological saline in front of the distal end of the insertion section of the endoscope as inserted into the blood vessel of the human subject. In contrast, the endoscopic image B shows the state in which the major area of the visual field of the endoscope is obstructed by the blood stream so that the inner wall of the blood stream is hardly observed.

In the case of the image A, a video signal corresponding to scanning lines as passed across the center of the image is converted to, as indicated by waveform 1 in FIG. 3, a color signal corresponding to the middle area of the blood stream and luminance signal nearly corresponding to the inner wall of the blood vessel, so that the luminance signal alone is obtained.

Figure 2:
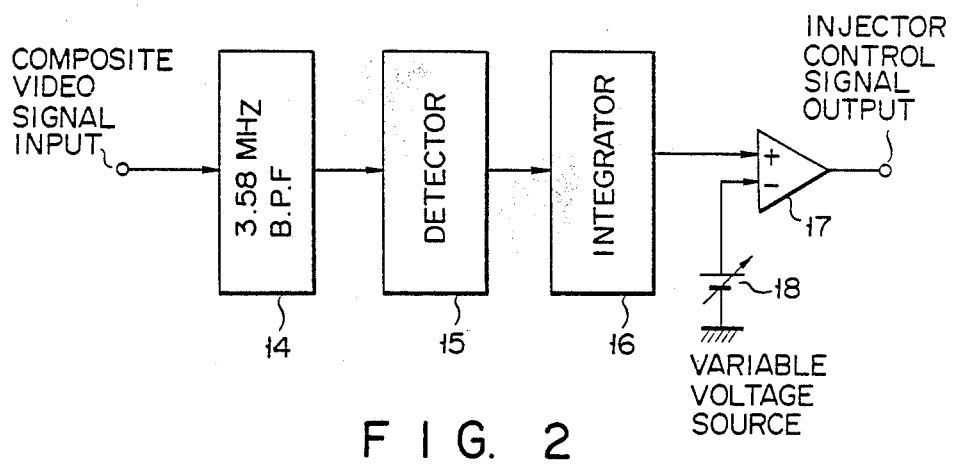
FIG. 2 is a block circuit diagram showing an endoscopic image analyzer.

The video signal corresponding to the aforementioned image is input to endoscopic analyzer 10 of such a type as shown in FIG. 2. Stated in more detail, the video signal is input to 3.58 MHz bandpass filter 14 and, in this case, the signal contains a color signal and synchronizing signal alone as indicated by waveform 2. The signal of waveform 2 is input to detector 15 and the detector delivers a signal having an envelope of waveform 2. A signal of waveform 3 is supplied to integrator 16 where it is integrated into waveform 4. The integration signal (waveform 4) is output to comparator 17 where it is compared with an output voltage $V_{comp}$ of variable power source 18.

Where the image picked up corresponds to the endoscopic image A, an amount of liquid (physiological saline) from injector device 11 has to be decreased because, at that time, the inner wall can adequately be observed on the endoscope. Thus the integration voltage $V_a$ is lower than the voltage $V_{comp}$ of variable voltage source 18. Comparator 17 compares the voltage $V_A$ with the voltage $V_{comp}$ to produce a low level signal $V_L$ as indicated by waveform 5 in FIG. 3. Injector device 11, upon receipt of the signal $V_L$, decreases a pressure level exerted on the physiological saline, so that an amount of liquid (phisiological saline) injected from channel opening 13 into the blood stream is decreased through liquid supply tube 12. It is, therefore, possible to suppress the injection level of any extra liquid into the blood stream.

Where, on the other hand, an image picked up corresponds to the image B, it is difficult to observe the inner wall of the blood vessel because the blood stream is not displaced around the distal end of the endoscope. At this time, the integration signal $V_B$ becomes greater than the output voltage of variable voltage source 18, so that the output of comparator 17 goes high ($V_H$). The injector device 11, upon receipt of the voltage signal $V_H$, serves to increase a pressure level exerted upon the tank liquid so that more liquid is injected from channel opening 13 into the blood stream past liquid supply tube 12. As a result, the blood stream is locally displaced, by the liquid, around the distal end of the endoscope to allow the inner wall of the blood vessel to be observed adequately on the endoscope.

In the aforementioned embodiment, since the output voltage $V_{comp}$ of variable voltage source 18 can properly be adjusted, the operator can freely select a boundary at which the output of the comparator goes high or low.

In the aforementioned embodiment, light source device 4, image processing device 8, endoscopic image analyzer 10, television monitor 9 and injector device 11 may be constructed as an integral unit. Although in the aforementioned embodiment bandpass filter 14 has been made at 3.58 MHz because the image signal obtained from camera 7 is based on the NTSC standard, the image signal may be based on the PAL standard. In this case the frequency of the bandpass filter becomes 4.43 MHz.

In the embodiment shown in FIG. 4, the output terminal of image processing device 8 is connected to synchronizing signal separation circuit 19. The synchronizing signal separation circuit separates vertical and horizontal synchronizing signals (Vsinc) and (Hsinc) from the video signal. The vertical and horizontal synchronizing signal output terminals of separation circuit 19 are connected to timing generator 20. Timing generator 20 is response to the vertical and horizontal synchronizing signals (Vsync and Hsync) to generate a high level signal during a period of time alone corresponding to the endoscopic image.

The output terminal of timing generator 20 is connected to a control terminal of switching circuit 21. Switching circuit 21 has its input terminal connected to the output terminal and its output terminal connected to 3.58 MHz bypass filter (BPF) 14.

In the aforementioned embodiment, timing generator 20, upon receipt of the vertical and horizontal synchronizing signals of separation circuit 19, delivers a timing signal, corresponding to the range of the endoscopic image in one frame (or one field) of the image, to switching circuit 21. Switching circuit 21, upon receipt of the timing signal from timing generator 20, is closed to allow the one-frame image signal of the range of the endoscopic image to be input to bandpass filter 14. The video signal which has been passed through bandpass filter 14 is delivered, past detector 15 shown in FIG. 2, to integrator 16 where it is integrated. The integration output is supplied to a comparator where, as in the previous embodiment, it is compared with a reference voltage $V_{comp}$. The result of comparison is utilized to control injector device 11.

Since, as set forth above, a video signal is analyzed within the range of the endoscopic image of one-frame, the image can be analyzed normally with high accuracy, irrespective of the size of the visual field of the endoscope which is occupied on the monitor screen.

It is to be noted that separation circuit 19, timing generator 20 and switching circuit 21 may be located in any proper location, provided that they are located between integrator 16 and the video signal output of image processing device 8.

FIG. 5 shows the circuit of endoscopic image analyzer 10 in another embodiment of this invention. In the circuit shown in FIG. 5, the G image signal of R, G and B image signals is delivered from image processing device 8 to integrator 16 whose output terminal is connected to the noninverting input terminal of operational amplifier 17 which is comprised of a comparator. Variable power source 18 is connected through a resistor to the noninverting input terminal of the operational amplifier, and the noninverting input terminal of the amplifier is connected further through another resistor to the output terminal of the amplifier. This circuit, including amplifier 17, constructs a known hysteresis circuit 22.

Figure 6:
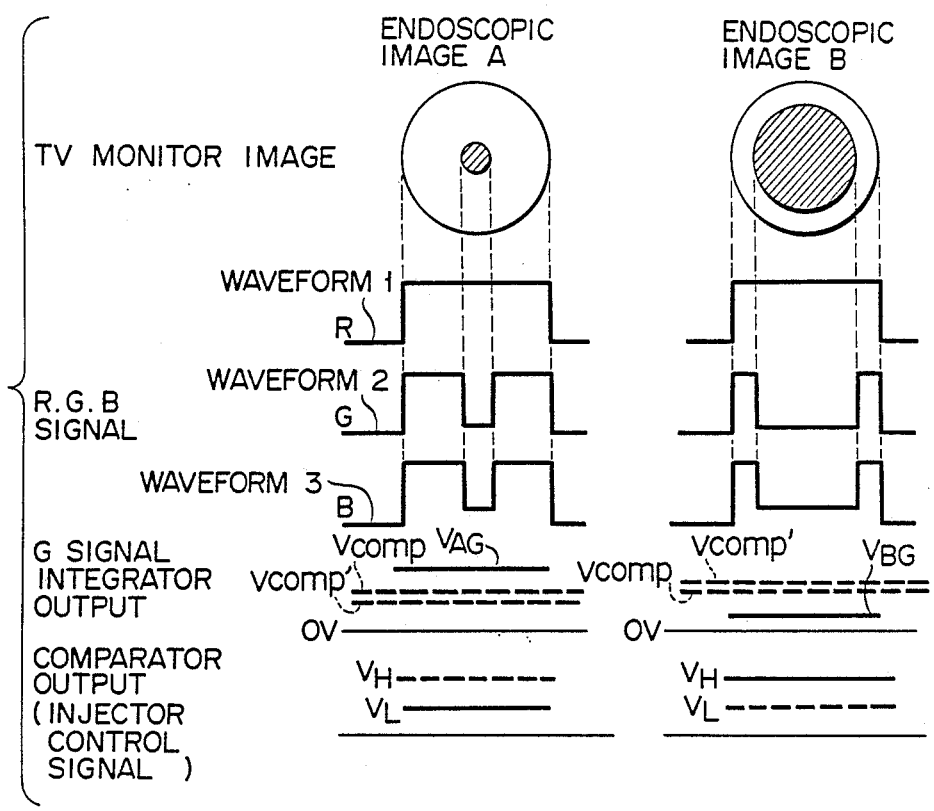
FIG. 6 is a time chart for explaining the operation of the intra-observation apparatus using the endoscopic image analyzer of FIG. 5.

In the circuit shown in FIG. 5, the video signals are delivered, as R, G and B signals, from image processing device 10, noting that the R, G and B signals represent waveforms 1, 2 and 3, respectively, in FIG. 6. As set forth above, a white signal is output as a mixed signal of R, G and B on the basis of the RGB system. As appreciated from the above, the white region corresponding to the inner wall of the blood vessel is output as a signal containing all of the R, G and B and the region near the middle of the blood stream is output as a signal whose G and B component levels are extremely lowered. Thus, the R, G and B signals are as indicated by waveforms 1, 2 and 3, respectively, in FIG. 6.

Of the R, G and B signals, the G signal is input to integrator 16 where it is integrated. The integrator supplies a $V_{AG}$ voltage signal, as an integration signal corresponding to the endoscopic image, to comparator 17. The voltage $V_{AG}$ is compared with the input voltage $V_{comp'}$ of the noninverting input terminal of comparator 17 by comparator 17. According to whether the output of comparator 17 is $V_L$ or $V_H$, the voltage $V_{comp'}$ is set lower or higher than the voltage $V_{comp}$ of variable voltage source 18 by a slight level. If $V_{AG} > V_{comp'}$, comparator 17 delivers a signal $V_L$ to injector device 11. As a result, injector device 11 is so operated as to lower the flow level of the liquid. The integration signal $V_{BG}$ corresponding to the endoscopic image B is output to comparator 17 where it is compared with the input voltage $V_{comp'}$ of the non-inverting input terminal of comparator 17. If $V_{BG} < V_{comp'}$, the output of comparator 17 is output to injector device 11. The injector device 11 is so operated as to increase the flow level of the liquid.

Although not only the G signal bus also the B signal may be used as a signal to be input to the integrator, if a xenon light source is used as the endoscopic light source, a light source beam is reflected as a blue beam from the inner surface of the blood vessel and, from this viewpoint, the G signal may be used so as to perform an exact image analysis.

In the embodiment shown in FIG. 5, the analyzer can be more simplified due to the analyzing of the R, G and B color signals than in the case where the video signal is analyzed. Since, according to this invention, the comparator is incorporated into the hysteresis circuit, a stable operation can be obtained when the injector control signal varies from the level $V_H$ to the level $V_L$ or vice versa.

Figure 7:
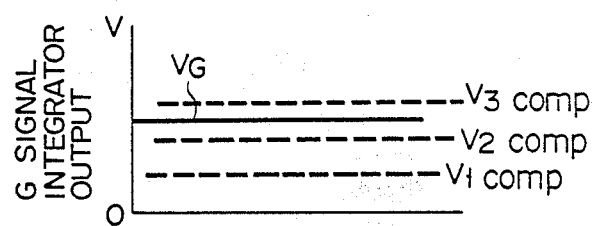
FIG. 7 is a graph showing a relation of reference and detection-voltages set in a plurality of levels on the embodiment of FIG. 3.

In the embodiment shown in FIG. 5, the output voltage of variable voltage source 18 is output as voltages $V_{1comp}$, $V_{2comp}$ and $V_{3comp}$ as shown in FIG. 7 and comparator 17 compares the input signal with these voltages. When $V_G < V_{1comp}$, $V_{1comp} < V_G < V_{2comp}$, $V_{2comp} < V_G < V_{3comp}$ and $V_{3comp} < V_G$, voltages $V_1$, $V_2$, $V_3$ and $V_4$ are output from comparator 17.

The integration voltage $V_G$ of integrator 16 is compared with the voltages $V_{1comp}$, $V_{2comp}$ and $V_{3comp}$, respectively, and when the result of comparison is $V_{2comp} < V_G < V_{3comp}$, comparator 17 delivers the output $V_3$ to injector device 11, allowing the liquid to be injected into the blood vessel in accordance with an amount of liquid, to be injected, corresponding to voltage $V_3$.

By setting the output voltage of variable voltage source 18 at the three levels as set out above, injector device 11 can vary the amount of liquid at four levels, so that the injector device quickly responds to a variation of the endoscopic image to permit the flow level of the liquid to be controlled. It is, therefore, possible to obtain a stabler endoscopic image. It is to be noted that the output voltage of variable voltage source 18 cannot be restricted to any of three levels.

In the embodiment shown in FIG. 5, the signal input to integrator 16 may be a composite video signal containing a color signal component corresponding to the blood and a luminance component as shown in FIG. 3, and so on. In this case, the output signal of integrator 16 is input to the inverting input terminal of comparator 17, whose non-inverting input terminal is coupled to variable voltage source 18.

Figure 8:
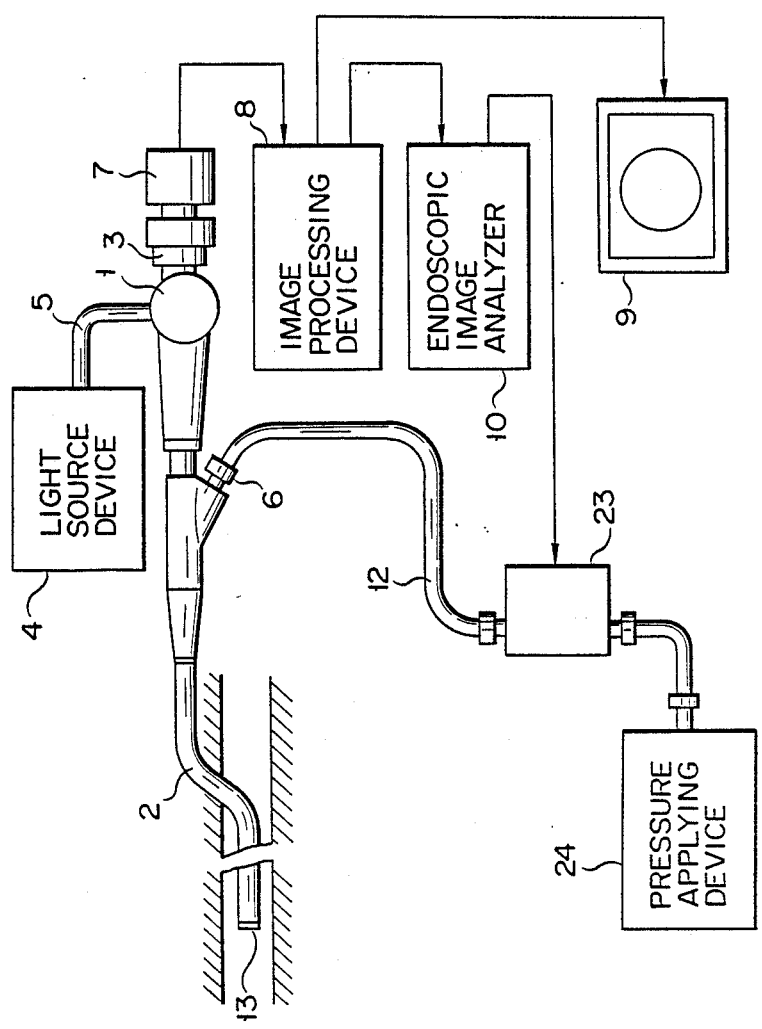
FIG. 8 is a block circuit diagram showing an intra-observation apparatus according to another embodiment of this invention.

In the embodiment shown in FIG. 8, pressure control valve 23 is provided between liquid supply tube 12 and pressure applying device 24 and operated in response to a comparator output signal from endoscopic image analyzer 11. Pressure applying device 24 includes a tank of physiological saline set normally under a predetermined pressure level.

In the intra-observation apparatus of this invention, pressure control valve 23 has its extent of opening controlled in accordance with a control signal from endoscopic image analyzer 10, whereby the liquid is injected from the liquid supply tube into the blood stream in accordance with the amount corresponding to the extent of opening of pressure control valve 23.

In the arrangement shown in FIG. 8, unlike the apparatus where the injector device is directly controlled, a proper amount of liquid can be supplied into the blood stream through the proper opening/closing operation of the pressure control valve, ensuring a simple liquid supply system. Furthermore, the repairing and exchanging of component parts can readily be made, since a control mechanism highly liable to fail is provided separate from the liquid supply source.

Figure 9:
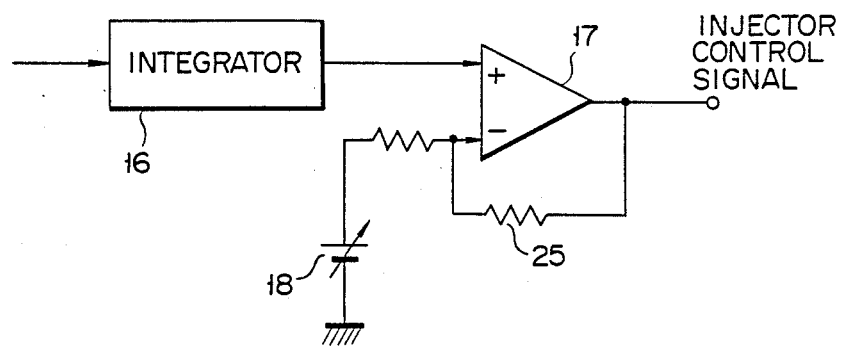
FIG. 9 shows a circuit diagram of an image analyzer used in another embodiment.
Figure 10:
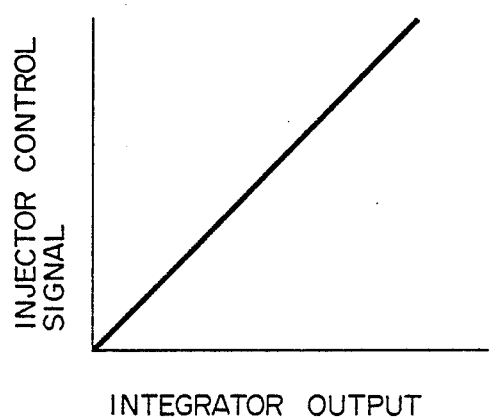
FIG. 10 is a graph showing an output characteristic of a non-inverting amplifier used in the image analyzer shown in FIG. 9.

FIG. 9 shows a circuit of analyzer 10 of another embodiment of this invention. The output terminal of integrator 16 is connected to the noninverting input terminal of operational amplifier 17. Variable voltage source 18 is connected through a resistor to the inverting input terminal of operational amplifier 17 and further through another resistor to the output terminal of operational amplifier 17. The circuit, including operational amplifier 17, constitutes known non-inverting amplifier 25. The output of the non-inverting amplifier is connected to injector 11.

An integration output of integrator 16 corresponding to an endoscopic image is input to noninverting amplifier 25 becomes a signal, which linearly corresponds to the integration output, and input to injector device 11. Injector device 11 linearly controls an amount of supplied water in accordance with the input signal.

Since analyzer 10 includes the non-inverting amplifier as a part of its circuit, an amount of water can be controlled, wholly in a servo control fashion, which linearly corresponds to the tonal color change of the endoscopic image. It is, therefore, possible to obtain a stabler endoscopic field of vision.

In the aforementioned embodiment, the region of interest can be photographed in interlock with the supply of the liquid with the light source as a flashing unit. In this case, the liquid is supplied to that region only during the photographing time, thus considerably saving an amount of liquid to be supplied. It is, therefore, possible to examine the inner wall of the blood vessel freely over a longer period of time.

The injector device may be coupled to the endoscope and a guide sheath for guiding the endoscope so that the transparent liquid can be injected into a gap between the guide sheath and the endoscope. Also, the injector device may be connected to a liquid flow tube such as a catheter, as provided in parallel with the endoscope, so that the transparent liquid is injected into the liquid flow tube.

According to this invention, the liquid can be supplied to the blood stream as small as required for local displacement of the blood stream by the liquid, there being a less risk that the liquid supply will cause a physiological disorder in the patient. In addition, an optimal amount of liquid is automatically and controllably determined in accordance with the region of interest, thus never requiring any operator's skill and any trial-and-error method. For this reason, the examination and treatment times can be reduced, alleviating the patient's burden. Furthermore, the insertion section of the endoscope can be narrowed because any extra structure is unnecessary. It is, therefore, possible to attach the intra-observation apparatus to the conventional endoscope for observation.

What is claimed is:

1. An intra-obseration apparatus, comprising:
   an endoscope having an eyepiece section and capable of observing an image of a tube-like passage;
   imaging means for converting an observation image to an image signal with the use of said endoscope;
   image analyzing means for evaluating a tonal color of said observation image from said image signal and for outputting an injection control signal corresponding to the tonal color; and
   control means for controlling an amount of liquid, to be injected, in response to said injection control signal.

2. An intra-observation apparatus according to claim 1, wherein said image analyzing means comprises:
   means for evaluating said tonal color of said image signal and for outputting a corresponding tonal color signal; and
   circuit means for comparing said tonal color signal obtained from said evaluating means with a reference value and for outputting said injection control signal, corresponding to the compared tonal signal, to said control means.

3. An intra-observation apparatus according to claim 1, wherein said image analyzing means comprises:
   filter means for filtering said image signal obtained from said imaging means;
   detecting means for converting said image signal passing through said filter means to an envelope signal;
   integrator means for integrating said envelope signal obtained from said detecting means and for outputting an integration signal corresponding to said tonal color; and
   circuit means for comparing said integration signal of said integrator means with said reference value and for outputting said injection control signal.

4. An intra-observation apparatus according to claim 3, wherein said filter means is comprised of a 3.58 MHz bandpass filter, when the image signal is based on a NTSC standard.

5. An intra-observation apparatus according to claim 2, wherein said circuit means is comprised of:
   a reference voltage source of generating a reference voltage as a reference value and a comparator for comparing an integration signal of said integrator means with said reference voltage.

6. An intra-observation apparatus according to claim 5, wherein said reference voltage source is comprised of a variable reference voltage arbitrrarily of controlling a reference voltage arbitrarily.

7. An intra-observation apparatus according to claim 2, wherein said circuit means delivers to said control means an injection control signal which corresponds to a variation of an integration signal relative to said reference value.

8. An intra-obsevation apparatus according to claim 1, wherein said imaging means delivers an image signal containing R, G and B signal components and said image analyzing means is comprised of integrator means for integrating one of B and G signal components of said image signal and for delivering an integration signal and hysteresis circuit means for outputting said injection control signal.

9. An intra-observation apparatus according to claim 1, wherein said image analyzing means is comprised of means for extracting an image signal corresponding to a range at an endoscopic image within a one-frame or one-field image, from said image signal, evaluating means for evaluating a tonal color from said image signal extracted from said image extracting means and for outputting a tonal color signal, and circuit means for comparing, with said reference value, a tonal color signal which is obtained from said evaluating means and for delivering to said control means an injection control signal which corresponds to the level of said tonal color signal relative to said reference value.

10. An intra-observation apparatus according to claim 9, wherein said image signal has vertial and horizontal signal components and said image extracting means is comprised of a synchronizing signal separation circuit for separating vertical and horizontal signal components from said image signal, means for outputting a timing signal, corresponding to the range of the endoscopic image within one frame or one field, in response to said vertical and horizontal synchronizing signal components obtained by said synchronizing signal separation circuit, and switching circuit means which is closed in response to said timing signal outputting means to conduct said image signal corresponding to the range of the endoscopic image to said evaluating means.

11. An intra-observation apparatus according to claim 1, wherein said control means is comprised of a tank filled with a transparent liquid and means for sending said transparent liquid into a region of interest at a flow level corresponding to said injection control signal.

12. An intra-observation apparatus according to claim 1, wherein said control means is comprised of means for containing a transparent liquid under a predetermined pressure level and a pressure control valve adapted to be opened in response to said control signal so as to supply said transparent liquid in said containing means into a region of interest at a flow level corresponding to said control signal.

13. An intra-observation apparatus according to claim 1, wherein said imaging means is a television camera attached to an eyepiece section of said endoscope.

14. An intra-observation apparatus according to claim 1, wherein said endoscope has a forceps channel and said control means is connected to said forceps to allow said transparent liquid to be sent into said forceps channel.

15. An intra-observation apparatus according to claim 1, wherein said image analyzing means comprises:
   means for integrating a signal corresponding to the image signal; and
   non-inverting amplifier means for amplifying an integrated signal obtained by said integrating means.

16. An intra-observation apparatus according to claim 3, wherein said filter means is comprised of a 4.43 MHz band pass filter when the image signal is based on a PAL standard.

17. An intra-observation apparatus according to claim 1, wherein said imaging means delivers the image signal containing a color signal component corresponding to a blood and a luminance signal component, and said image analyzing means is comprised of integrator means for integrating the image signal including said color and luminance signal components to output an integration signal, and hysteresis circuit means for outputting said injection control signal.

* * * * *

UNITED STATES PATENT AND TRADEMARK OFFICE
CERTIFICATE OF CORRECTION

PATENT NO. : 4,827,907

DATED : May 9, 1989

INVENTOR(S) : Yoshiro TASHIRO

It is certified that error appears in the above-identified patent and that said Letters Patent is hereby corrected as shown below:

```
Title page: item 73 "Teac Optical Co.", Ltd. should
     read -- Olympus Optical Co., Ltd. --
```

Signed and Sealed this

Eighth Day of January, 1991

*Attest:*

HARRY F. MANBECK, JR.

*Attesting Officer*     *Commissioner of Patents and Trademarks*